(12) United States Patent
Jafarkhani et al.

(10) Patent No.: US 9,875,581 B2
(45) Date of Patent: Jan. 23, 2018

(54) AUTOMATED 3D RECONSTRUCTION OF THE CARDIAC CHAMBERS FROM MRI OR ULTRASOUND

(71) Applicant: The Regents of the University of California, Oakland, CA (US)

(72) Inventors: Hamid Jafarkhani, Irvine, CA (US); Mahdi Hajiaghayi, Irvine, CA (US); Elliott Groves, Castro Valley, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 170 days.

(21) Appl. No.: 14/929,806

(22) Filed: Nov. 2, 2015

(65) Prior Publication Data

US 2016/0140751 A1   May 19, 2016

Related U.S. Application Data

(60) Provisional application No. 62/073,688, filed on Oct. 31, 2014.

(51) Int. Cl.
*G06K 9/00* (2006.01)
*G06K 9/40* (2006.01)
(Continued)

(52) U.S. Cl.
CPC ............ *G06T 19/20* (2013.01); *A61B 5/0044* (2013.01); *A61B 5/055* (2013.01); *A61B 8/0883* (2013.01); *A61B 8/466* (2013.01); *A61B 8/483* (2013.01); *G06T 7/12* (2017.01); *G06T 7/149* (2017.01); *A61B 8/5223* (2013.01);
(Continued)

(58) Field of Classification Search
None
See application file for complete search history.

(56) References Cited

U.S. PATENT DOCUMENTS 6,201,543 B1 * 3/2001 O'Donnell ........... G06K 9/6207
345/420
7,095,890 B2 * 8/2006 Paragios ................... G06T 7/12
382/128

(Continued)

OTHER PUBLICATIONS

Bresson, et al. 2006 "A Variational Model for Object Segmentation Using Boundary Information and Shape Prior Driven by the Mumford-Shah Functional" *International Journal of Computer Vision* 68(2): 145-162.

(Continued)

*Primary Examiner* — Matthew Bella
*Assistant Examiner* — Jose M Torres
(74) *Attorney, Agent, or Firm* — Knobbe, Martens, Olson & Bear, LLP

(57) ABSTRACT

The disclosure relates to a method of automatically producing a three-dimensional (3D) segmentation of a heart chamber, the method comprising: obtaining data sets from cardiac magnetic resonance imaging (MRI) or ultrasound, generating a 3D segmentation of the heart chamber from the data sets using an active contour method, modifying the 3D segmentation by adding a plurality of intra-chamber structures; and identifying an enclosing myocardium using the 3D segmentation generated by the method.

13 Claims, 12 Drawing Sheets

(51) Int. Cl.
| | |
|---|---|
| G06T 19/20 | (2011.01) |
| A61B 5/055 | (2006.01) |
| A61B 5/00 | (2006.01) |
| A61B 8/08 | (2006.01) |
| A61B 8/00 | (2006.01) |
| G06T 7/12 | (2017.01) |
| G06T 7/149 | (2017.01) |

(52) U.S. Cl.
CPC . *A61B 2576/02* (2013.01); *G06T 2207/10088* (2013.01); *G06T 2207/10132* (2013.01); *G06T 2207/20116* (2013.01); *G06T 2207/30048* (2013.01); *G06T 2219/2021* (2013.01)

(56) References Cited

U.S. PATENT DOCUMENTS

| | | | | |
|---|---|---|---|---|
| 2010/0215238 | A1* | 8/2010 | Lu | G06T 7/12 382/131 |
| 2012/0099799 | A1* | 4/2012 | Fujiwara | G06T 7/12 382/203 |
| 2012/0281895 | A1* | 11/2012 | Chono | A61B 8/461 382/128 |

OTHER PUBLICATIONS

Chan, et al. 2001 "Active Contours Without Edges" *IEEE Transactions on Image Processing* 10(2): 266-277.
Codella, et al. 2008 "Left Ventricle: Automated Segmentation by Using Myocardial Effusion Threshold Reduction and Intravoxel Computation at MR Imaging" *Radiology* 248(3): 1004-1012.
Codella, et al. 2010 "Rapid and Accurate Left Ventricular Chamber Quantification Using a Novel CMR Segmentation Algorithm: A Clinical Validation Study" *Journal of Magnetic Resonance Imaging* 31: 845-853.
Dempster, et al. 1977 "Maximum Likelihood from Incomplete Data via the EM Algorithm" *Journal of the Royal Statistical Society* 39(1): 1-38.
Frangi, et al. 2001 "Three-Dimensional Modeling for Functional Analysis of Cardiac Images: A Review" *IEEE Transactions on Medical Imaging* 20(1): 2-25.
El Berbari, et al. 2007 "An automated myocardial segmentation in cardiac MRI" *Proceedings of the 29th Annual International Conference of the IEEE EMBS*: 4508-4511.
Heimann, et al. 2009 "Statistical shape models for 3D medical image segmentation: A review" *Medical Image Analysis* 13: 543-563.
Goshtasby, et al. 1995 "Segmentation of Cardiac Cine MR Images for Extraction of Right and Left Ventricular Chambers" *IEEE Transactions on Medical Imaging* 14(1): 56-64.
Groves, et al. 2007 "Quantitative Analysis of ECG-Gated High-Resolution Contrast-Enhanced MR Angiography of the Thoracic Aorta" *Vascular Imaging* 188: 522-528.
Grosgeorge, et al. 2011 "Automatic cardiac ventricle segmentation in MR images: a validation study" *Int J CARS* 6: 573-581.
Janik, et al. 2008 "Effects of papillary muscles and trabeculae on left ventricular quantification: increased impact of methodological variability in patients with left ventricular hypertrophy" *Journal of Hypertension* 26: 1677-1685.
Jolly 2006 "Automatic Segmentation of the Left Ventricle in Cardiac MR and CT Images" *International Journal of Computer Vision* 70(2): 151-163.
Kadir, et al. 2010 "Automatic Left Ventricle Segmentation in T2 Weighted CMR Images" *AISC* 84: 247-254.
Kass, et al. 1988 "Snakes: Active Contour Models" *International Journal of Computer Vision*: 321-331.
Kaus, et al. 2004 "Automated segmentation of the left ventricle in cardiac MRI" *Medical Image Analysis* 8: 245-254.
Lima, et al. 2004 "Cardiovascular Magnetic Resonance Imaging: Current and Emerging Applications" *Journal of the American College of Cardiology* 44(6): 1164-1171.
Lorenzo-Valdés, et al. 2003 "Segmentation of 4D Cardiac MR Images Using a Probabilistic Atlas and the EM Algorithm" *LNCS* 2878: 440-450.
Lu, et al. 2009 "Automatic Image-Driven Segmentation of Left Ventricle in Cardiac Cine MRI"; pp. 1-8.
Lynch, et al. 2006 "Automatic segmentation of the left ventricle cavity and myocardium in MRI data" *Computers in Biology and Medicine* 36: 389-407.
Malladi, et al. 1995 "Shape Modeling with Front Propagation: A Level Set Approach" *IEEE Transactions on Pattern Analysis and Machine Intelligence* 17(2): 158-175.
Mille, et al. 2007 "Segmentation and tracking of the left ventricle in 3D MRI sequences using an active surface model" *IEEE International Symposium on Computer-Based Medical Systems*: 1-6.
Mitchell, et al. 2002 "3-D Active Appearance Models: Segmentation of Cardiac MR and Ultrasound Images" *IEEE Transactions on Medical Imaging* 21(9): 1167-1178.
Mora, et al. 2006 "2D Local Heart Motion Estimation Using Level Sets and Hierarchical B-Splines" *Computers in Cardiology* 33: 513-516.
Pednekar, et al. 2006 "Automated Left Ventricular Segmentation in Cardiac MRI" *IEEE Transactions on Biomedical Engineering* 53(7): 1425-1428.
Pluempitiwiriyawej, et al. 2005 "STACS: New Active Contour Scheme for Cardiac MR Image Segmentation" *IEEE Transactions on Medical Imaging* 24(5): 593-603.
Sardanelli, et al. 2008 "Segmentation of Cardiac Cine MR Images of Left and Right Ventricles: Interactive Semiautomated Methods and Manual Contouring by Two Readers With Different Education and Experience" *Journal of Magnetic Resonance Imaging* 27: 785-792.
Sussman, et al. 1994 "A level set approach for computing solutions to incompressible two-phase flow" *Journal of Computational Physics* 114: 146-159.
Ulén, et al. 2012 "An Efficient Optimization Framework for Multi-Region Segmentation based on Lagrangian Duality" *IEEE*; pp. 1-11.
Van Assen, et al. 2006 "SPASM: A 3D-ASM for segmentation of sparse and arbitrarily oriented cardiac MRI data" *Medical Image Analysis* 10: 286-303.
Wang, et al. 2014 "TouchCut: Fast image and video segmentation using single-touch interaction" *Computer Vision and Image Understanding* 120: 14-30.
Xu, et al. 2000 "Image Segmentation Using Deformable Models" pp. 129-174.
Yuan, et al. 2002 "Contrast-Enhanced High Resolution MRI for Atherosclerotic Carotid Artery Tissue Characterization" *Journal of Magnetic Resonance Imaging* 15: 62-67.

* cited by examiner

AUTOMATED 3D RECONSTRUCTION OF THE CARDIAC CHAMBERS FROM MRI OR ULTRASOUND

INCORPORATION BY REFERENCE TO ANY PRIORITY APPLICATIONS

This application claims priority U.S. Provisional Application No. 62/073,688 filed on Oct. 31, 2014. Any and all applications for which a foreign or domestic priority claim is identified in the Application Data Sheet as filed with the present application are hereby incorporated by reference under 37 CFR 1.57.

BACKGROUND

Cardiac magnetic resonance imaging (CMR) is a valuable tool that provides important information for diagnosis and evaluation of cardiac anatomic abnormalities, and cardiovascular disease (Frangi A F, Niessen W J, Viergever M A. Three-dimensional modeling for functional analysis of cardiac images, a review. *Medical Imaging, IEEE Transactions on* 2001; 20(1):2-5). CMR is a safe modality that does not require ionizing radiation or iodinated contrast but delivers images with high spatial and temporal resolution (Yuan C, Kerwin W S, Ferguson M S, et al. Contrast-enhanced high resolution MRI for atherosclerotic carotid artery tissue characterization. *Journal of Magnetic Resonance Imaging* 2002; 15(1): 62-67; Lima J A, Desai M Y. Cardiovascular magnetic resonance imaging: current and emerging applications. *Journal of the American College of Cardiology* 2004; 44(6): 1164-1171). One important aspect of CMR imaging is its potential for segmentation of the cardiac chambers to determine clinical information such as ejection fraction and chamber volumes (Heimann T, Meinzer H-P. Statistical shape models for 3D medical image segmentation: A review. *Medical Image Analysis* 2009; 13(4): 543-563). Currently many of the commercially available software platforms for CMR post-processing either provide suboptimal automated segmentation or require a substantial amount of manual segmentation support from the user, resulting in significant methodological variability (Janik M, Cham M D, Ross M I, et al. Effects of papillary muscles and trabeculae on left ventricular quantification: increased impact of methodological variability in patients with left ventricular hypertrophy. *Journal of hypertension* 2008; 26(8):1677-1685). Additionally, manual segmentation is time consuming, and requires dedicated operator training that makes it inefficient due to the extent of information in CMR images.

Most cardiac segmentation techniques treat "2D segmentation" and "3D multiplanar reconstruction" as two separate processes (Jolly M-P. Automatic segmentation of the left ventricle in cardiac MR and CT images. *International Journal of Computer Vision* 2006; 70(2): 151-163). These processes achieve volumetric reconstruction by first applying a 2D segmentation approach independently for each slice, and then volumizing these 2D segmented image stacks into 3D objects. This procedure only considers volumizing a particular stack. Therefore, some important details of the object would be lost during the procedure; thus the resultant objects usually possess rough surfaces.

Although there are some methods to automate consecutive "2D segmentation" and "3D multiplanar reconstruction" steps, this approach fails to exploit the benefit of a true, 3D volumizing technique. Additionally, most segmentation approaches in 2D cannot readily handle cases where an object of interest (e.g., papillary muscles) appears to be separated into several cross-sections (i.e., non-convex object). This separation and discontinuity commonly can be seen in CMR images, which incur further challenges in 2D segmentation.

The need for an efficient, accurate, and automated segmentation method has stimulated a large body of work in automated 3D CMR segmentation. Among these studies, early attempts at thresholding (Goshtasby A, Turner D A. Segmentation of cardiac cine MR images for extraction of right and left ventricular chambers. *Medical Imaging, IEEE Transactions on* 1995; 14: 56-64) were followed by the popular pixel classification (Pednekar A, Kurkure U, Muthupillai R, Flamm S, Kakadiaris I A. Automated left ventricular segmentation in cardiac MRI. *Biomedical Engineering, IEEE Transactions on* 2006; 53(7): 1425-1428; Lynch M, Ghita O, Whelan P F. Automatic segmentation of the left ventricle cavity and myocardium in MRI data. *Computers in Biology and Medicine* 2006; 36(4): 389-407), active contour approaches (Xu C, Pham D L, Prince J L. Image segmentation using deformable models. *Handbook of medical imaging* 2000; 2:129-174; Grosgeorge D, Petitjean C, Caudron J, Fares J, Dacher J-N. Automatic cardiac ventricle segmentation in MR images: a validation study. *International journal of computer assisted radiology and surgery* 2011; 6(5): 573-581) and region based approaches (Grosgeorge et al. (supra); Mule J, Bone R, Makris P, Cardot H. Segmentation and tracking of the left ventricle in 3D MRI sequences using an active surface model. In *Computer-Based Medical Systems, Twentieth IEEE International Symposium on;* 2007. p. 257-262). However, none of these singular approaches has resulted in an accurate and fast segmentation algorithm that requires no prior statistical model.

SUMMARY OF THE INVENTION

Disclosed are a new and useful apparatus and method for reconstructing cardiac chambers in 3D using an MRI or ultrasound image. Specifically, the methodologies utilize a segmentation algorithm, which automatically reconstructs raw cardiac MRI or Ultrasound data to a 3D model (i.e., direct volumetric segmentation), without relying on any prior statistical knowledge, making it widely applicable and useful for many clinical applications.

Some embodiments relate to a method of automatically producing a three-dimensional (3D) segmentation of a heart chamber, the method comprising:
  (a) obtaining data sets from cardiac magnetic resonance imaging (MRI) or ultrasound,
  (b) generating a 3D segmentation of the heart chamber from the data sets using an active contour method,
  (c) modifying the 3D segmentation by adding a plurality of intra-chamber structures; and
  (d) identifying an enclosing myocardium using the 3D segmentation generated in step (b).

In some methods, generating the 3D segmentation of the heart chamber from the MRI or ultrasound data sets includes minimizing an energy function, $E(\Phi)$, when a contour lies on a boundary of the heart chamber, wherein $E(\Phi)$ is defined as $$E(\Phi) = E_{int}(\Phi) + E_{ext}(\Phi),$$

wherein $E_{int}$ is the internal energy function and $E_{ext}$ is the external energy function of the heart chamber in a 3D domain.

In some embodiments, minimizing the energy function, $E(\Phi)$ includes using an external energy function, $E_{ext}(\Phi)$, defined as $$E_{ext}(\Phi) = w_2 E_{reg} + w_3 E_{edge} + w_4 E_{geom}$$

wherein $E_{reg}$ is a region-based term, $E_{edge}$ is an edge-based term, $E_{geom}$ is a geometric term, and where $w_2$, $w_3$, and $w_4$ are a plurality of weighting parameters.

In some embodiments the MRI or ultrasound data sets comprise a plurality of short-axis cardiac magnetic resonance images, long-axis cardiac magnetic resonance images, sagittal MRI images, coronal MRI images, axial MRI images, or any combination thereof.

Some embodiments further include normalizing the MRI or ultrasound data sets and reusing the same weighting parameters across the entire MRI or ultrasound data set.

In some embodiments, modifying the 3D estimation with a plurality of cardiac substructures includes:
identifying a plurality of points on a convex hull of the 3D segmentation;
computing a centroid for the plurality of points;
calculating the radius and angle of the plurality of points on the convex hull with respect to the centroid to produce cylindrical coordinates for the plurality of points on the convex hull; and
interpolating the cylindrical coordinates to produce a closed convex curve which includes the plurality of cardiac substructures.

In some embodiments, identifying an enclosing myocardium using the 3D segmentation includes removing a portion of endocardium of the cardiac structure from the 3D segmentation and refilling the 3D estimation with a color representing the myocardium of the cardiac structure in its place as the distance from the centroid is increased.

In some embodiments, generating a 3D segmentation of the cardiac structure from the MRI or ultrasound data sets includes simultaneously segmenting the MRI or ultrasound data sets and reconstructing 3D images therefrom.

In some embodiments, the heart chamber is selected from the group consisting of the left ventricle, the right ventricle, the left atrium and the right atrium.

In some embodiments, modifying the 3D segmentation by adding a plurality of intra-chamber structures includes adding papillary muscles to a reconstructed volume.

In some embodiments, the papillary muscles are in the left ventricle.

In some embodiments, a 3D contour of the heart chamber is non-covex, wherein a line connecting any two points inside the contour is not necessarily inside the contour, the method including identifying points on a convex hull of a contour, computing a centroid value by averaging over all the points, wherein the centroid point is used as a center of cylindrical coordinates and a radius and angle of all points on the convex hull are calculated based on a new coordinate system, wherein a new set of points constructs a closed convex curve that best approximates the non-convex contour.

Some embodiments include further extracting the enclosing myocardium from the rest of the 3D segmentation of the heart chamber.

Some embodiments include calculating a volume of the heart chamber.

Some embodiments relate to a computer readable medium containing software instructions for preforming the methods disclosed herein.

DETAILED DESCRIPTION

We have developed and tested a fast, automated 3D segmentation tool for cardiac Magnetic Resonance Imaging (MRI) or cardiac Ultrasound imaging. The segmentation algorithm automatically reconstructs raw cardiac MRI or Ultrasound data to a 3D model (i.e., direct volumetric segmentation), without relying on any prior statistical knowledge, making it widely applicable and useful for many clinical applications.

To overcome limitations of previous methodologies, the current invention utilizes emerging principles in image processing to develop a true 3D reconstruction technique without the need for training datasets or any user-driven segmentation. This was accomplished by developing an automatic segmentation framework that exploits the benefit of full volumetric imaging in an anatomically natural way. Because the current method does not rely on prior statistical knowledge, it offers dramatically more malleability than current algorithms by being broadly applicable across differing pathologies and cardiac magnetic resonance (CMR) imaging techniques.

Through the work described here, a fast, reliable, accurate 3D segmentation algorithm has been developed. This novel algorithm delivers a high segmentation performance when compared to manual segmentation and may in fact be superior given the fact that manual segmentation has inherent limitations. Additionally we show an improved performance when compared to other segmentation algorithms.

The current method performs simultaneous segmentation and three-dimensional reconstruction, which can also use any standard MRI images (axial, coronal, or sagittal), along with both short- and long-axis CMR data. Therefore, this tool produces 3D segmentations that are considerably smoother than those created from the currently available tools based on multiplanar reconstruction of two-dimensional segmented planes. The current method also minimizes user interaction to only a single click on the chamber of interest in one slice.

Figure 1:
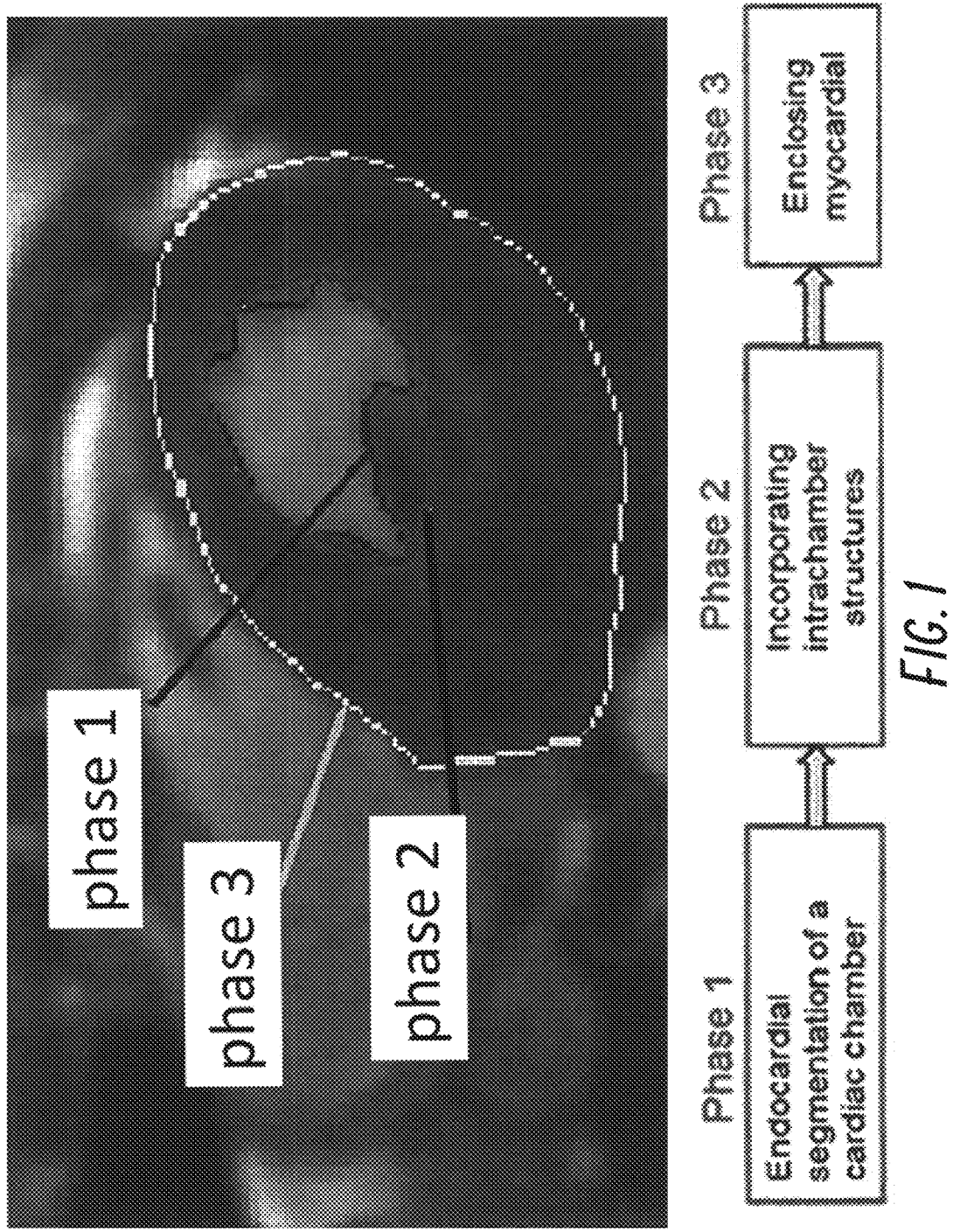
FIG. 1: Three steps (phases) of the segmentation method: Step 1 segments the endocardial layer of a cardiac chamber; Step 2 incorporates intra-chamber structures; Step 3 defines the enclosing myocardium.

The input to the algorithm is a sequence of either short- or long-axis CMR images, and the output is a refined point cloud representing the cardiac chamber being segmented. A unique feature of this algorithm is that it can accommodate any standard sagittal, coronal, and axial MRI images, even those not obtained as a dedicated CMR. The current algorithm can additionally incorporate data from all the orthogonal imaging stacks, providing a smoother and at the same time, more anatomically accurate segmentation result. This method is carried out over three consecutive steps; in the first step, the algorithm generates a 3D estimation of a heart chamber (e.g., left ventricle (LV)) using an active contour method. In the second step, it modifies the result by adding intra chamber structures (e.g., papillary muscles in the left ventricle) that many automated segmentation algorithms usually exclude from the chamber. During the final step, the algorithm identifies the enclosing myocardium using the 3D segmentation utilized for the first phase with some modifications. FIG. 1 shows the three steps in a cross-section of a 3D image. The three steps of the segmentation method include step I which segments the endocardial layer of a cardiac chamber, step II which incorporates intra-chamber structures, and then step III which defines the enclosing myocardium. Each step is further elaborated upon below.

Step I: 3D Active Contour Segmentation 3D active contours are dynamic surfaces that evolve and move toward the object of interest and eventually lie on its edges. To mathematically represent such a surface in a 3D domain, we employ signed distance function (SDF) $\Phi(v)$ for all voxels $v=(x,y,z)$ (Malladi R, Sethian J A, Vemuri B C. Shape modeling with front propagation: A level set approach. Pattern Analysis and Machine Intelligence, *IEEE Transactions on* 1995; 17(2): 158-175). Using this function for a closed contour returns negative values for the voxels inside the contour and positive values for the voxels outside. Evolution of the active contour is driven by minimizing an energy function $E(\Phi)$ designed to reach its minimum when the contour lies on the boundary of the object of interest. The $E(\Phi)$ generally includes two components:

$$E(\Phi)=E_{int}(\Phi)+E_{ext}(\Phi) \qquad (1)$$

where Eint and Eext are the internal and external energy functions, respectively. Eint, whose minimization shrinks the contour's surface, plays a regularization role to control the contour's smoothness. Let $\Omega$ be the image domain and I(v) denote the color intensity at voxel v. The internal energy function for a SDF $\Phi$ is given by Van Assen et al. (Van Assen H C, Danilouchkine M G, Frangi A F, et al. SPASM: a 3D-ASM for segmentation of sparse and arbitrarily oriented cardiac MRI data. *Medical Image Analysis* 2006; 10(2):286-303):

$$E_{int}(\Phi)=w_1\Sigma_{v\in\Omega}|\nabla H(\Phi(v))| \qquad (2)$$

where $\nabla$ and $|\cdot|$ denote gradient and absolute value operators, respectively. Moreover, $H(x)$: $R\rightarrow R$ is the Heaviside function with $H(x)=1$ for $x>0$ and $H(x)=0$ otherwise. As a result, $H(\Phi(v))$ is zero inside and 1 outside of the contour, and thus $|\nabla H(\Phi(v))|=1$ at the border and 0 elsewhere. $E_{ext}$ is a data-driven term that provides information about the object boundaries and plays a role as driver. For example, for segmentation of the left ventricle, we use the following external energy function:

$$E_{ext}(\Phi)=w_2 E_{reg}+w_3 E_{edge}+w_4 E_{geom} \qquad (3)$$

which is a combination of the region-based ($E_{reg}$), edge-based ($E_{edge}$) and geometric terms ($E_{geom}$) to be introduced shortly. $w_1$, $w_2$, $w_3$ and $w_4$ are the weighting parameters, summed to 1, that must be carefully chosen for an image. While the effect of weighting parameters can be negligible for some object segmentation, it seems these parameters are more sensitive in cardiac MRI segmentation. No quantitative analysis or straightforward strategy currently exists to yield the weighting parameters for segmentation. In the current method, we often pursued a trial and error approach to obtain these parameters. However, once the optimal weighting parameters are found for one cardiac MRI image, they can be used for other images as well without significantly compromising the performance. Moreover, for these parameters to yield better results in other images, we introduced the histogram matching technique as explained in further detail below.

The region-based term (Ereg) from the equation above calculates how likely a voxel v is to belong to foreground or background given its color density (Pluempitiwiriyawej C, Moura J M F, Wu Y-J L, Ho C. STACS: new active contour scheme for cardiac MR image segmentation. *Medical Imaging, IEEE Transactions on* 2005; 24(5): 593-603):

$$Ereg=-\Sigma_{v\in\Omega}(\log p(I(v)|\Omega_F)(1-H(\Phi))+\log p(I(v)|\Omega_B) H(\Phi)) \qquad (4)$$

where $P(\cdot|\Omega_F)$ and $P(\cdot|\Omega_B)$ are foreground and background probability distribution functions (PDF), respectively. If they are not known a priori, they are replaced by the PDF of inside and outside of the active contour usually modeled by Gaussian distribution with different means and variances. As the contour evolves, the means and variances are both updated. Edge-based term ($E_{edge}$) detects the edges of objects (Kass M, Witkin A, Terzopoulos D. Snakes: Active contour models. *International Journal of Computer Vision* 1988; 1(4): 321-331):

$$E_{edge}=\Sigma_{v\in\Omega}g(I(v))|\nabla H(\Phi)| \qquad (5)$$

where g(I) can be any function whose minimum occurs at the edge of the object of interest (Malladi R, Sethian J A, Vemuri B C. Shape modeling with front propagation: A level set approach. Pattern Analysis and Machine Intelligence, *IEEE Transactions on* 1995; 17(2): 158-175). The geometric term ($E_{geom}$) sets geometrical constraints on the active contour. For instance, a symmetric constraint on the LV'S short-axis can be defined as:

$$E_{geom} = \left| \frac{\sum_{v \in \Omega} (x-x_0)(1-H(\Phi))}{\sum_{v \in \Omega} (1-H(\Phi))} \right| + \left| \frac{\sum_{v \in \Omega} (y-y_0)(1-H(\Phi))}{\sum_{v \in \Omega} (1-H(\Phi))} \right| \quad (6)$$

A similar term has been introduced (Wang T, Han B, Collomosse J. TouchCut: Fast image and video segmentation using single-touch interaction Computer Vision and Image Understanding 2013; In process). This function calculates the x and y spatial deviation of the geometrical center of the active contour C from the centroid point's $x_0$ and $y_0$ dimensions. How the centroid point is obtained is described in further detail below. The active contour problem seeks a unique contour denoted by C* (or equivalently $\Phi$*), which lies on the boundary of the object of interest. This problem translates into the underlying minimization problem over $\Phi$:

$$\Phi^* = \arg\min_{\Phi}(E_{int}(\Phi) + E_{ext}(\Phi)) \quad (7)$$

for which we employ the gradient descent algorithm to solve. Both $E_{ext}$ and $E_{int}$ are functionals, and their derivatives, which are required for the gradient descent algorithm are calculated using Euler-Lagrange equality (Elsgolc L. Calculus of Variations: Courier Dover Publications 1963). They must be computed for each voxel $A \in \Omega$, and therefore are usually expressed as 3D matrices. In this case, the gradient descent starts with a 3D initialization matrix for $\Phi^0$ (v), $v \in \Omega$. To construct the initial distance function $\Phi^0$, a 2D slice from the middle of the CMR image stack is displayed to the user requesting the user to click on a point near the center of the left ventricle. Centered at that point, we consider a contour ball whose respective signed distance function forms $\Phi^0$. The x and y dimensions of this point can be also used as $(x_0, y_0)$ for the geometric term.

Each iteration of the gradient descent algorithm updates the function $\Phi$ for each voxel. However, this update may not maintain the sign distance property of $\Phi$. For this purpose, we must frequently reinitialize (Sussman M, Smereka P, Osher S. A level set approach for computing solutions to incompressible two-phase flow. *Journal of Computational physics* 1994; 114(1): 146-159). The final $\Phi^*$ yields the final contour C*. As it is not mathematically simple to represent a 3D contour, we use SDF function, $\Phi$, which has one-to-one mapping with C. This mapping is as follows, or given $\Phi$, all the points that have zero value specify the contour. That is, $$C = \{v \in R^3, \Phi(v) = 0\} \quad (8)$$

Figure 2:
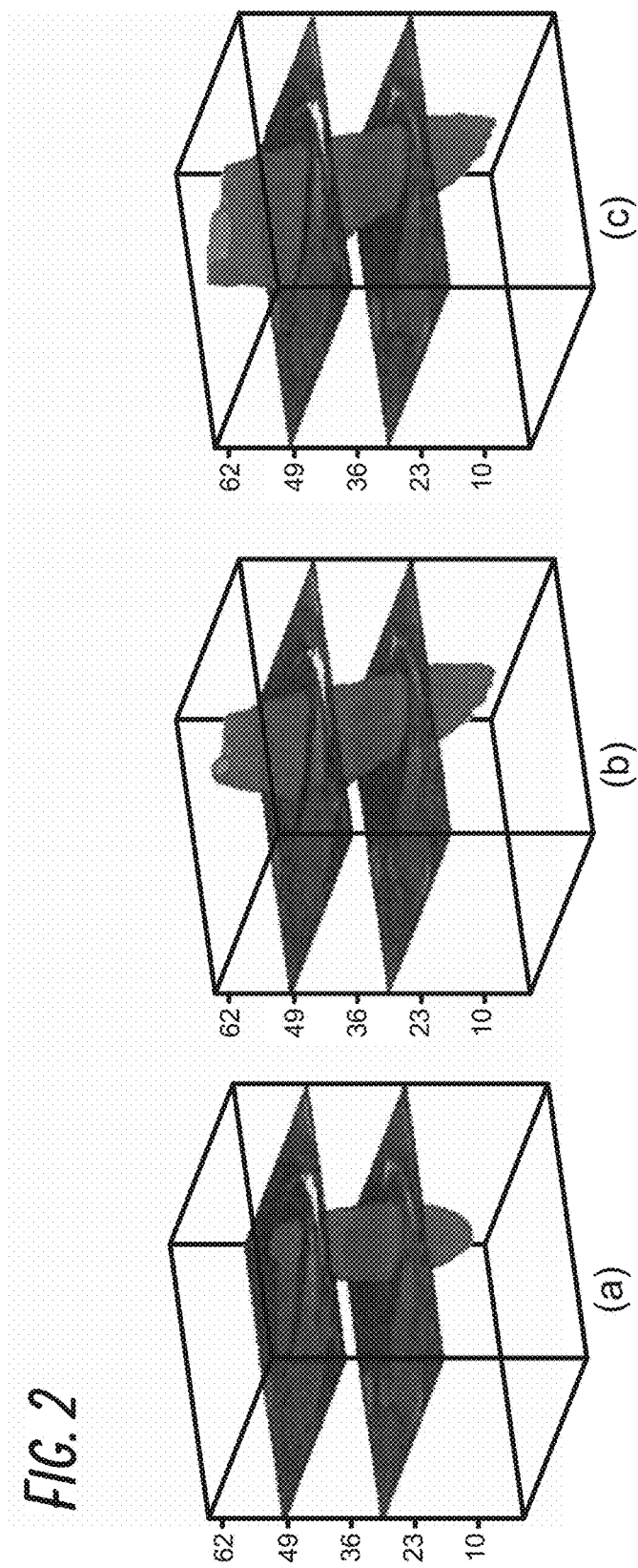
FIG. 2: Illustration of the left ventricular contour evolution: (a) in early iteration; (b) mid iteration; and (c) final iteration of gradient descent algorithm.

Hence, once we find $\Phi^*$, we can use this mapping to obtain C*. FIG. 2 depicts the evolution of the LV's 3D contour in the first phase of our algorithm for a long-axis axial 3D image of the LV. FIGS. 2A, 2B, and 2C show an early iteration, a mid iteration, and a final iteration of the gradient descent algorithm, respectively. This phase does not include the papillary muscles within the LV volume.

The weighting parameters $w_1, \ldots, w_4$ play a paramount role in achieving a desirable segmentation result. For example, high $w_1$ favors the internal energy term that excessively smoothes the shape. The optimal weights for an image are conventionally obtained through a trial and error procedure. This procedure can be tedious for a large database to be segmented. In that case, the weights are usually selected based on the inspection of a few images and kept fixed for the rest of images. However, as the characteristics of MR images vary across the database, the optimal weights from one image to another might be very different. For instance, a noisy image with low contrast between chambers requires higher $w_1$ and $w_3$ and lower $w_2$ comparing to an image with high contrast in which lower $w_1$ results in better segmentation result. It is evident, that similar images share the same optimal parameters. Hence, the optimal weighting parameters obtained for one image (i.e., reference image) can be used for a new image as long as we find a way to make these two images similar, or in another word normalized. We use histogram matching as a normalizing approach for this purpose. For a new image, we first match its signal intensity histogram to the reference image, and then use the same weights of reference image for the new image. The details of histogram matching can be found in Gonzalez et al. (Gonzalez R C, Woods R E. Digital image processing, 2nd. SL: Prentice Hall 2002). We observe that using the histogram matching with fixed weights significantly improves the performance of segmentation algorithm compared to the case with fixed weighting parameters and no normalization.

Step II: Intra-Chamber Inclusion Using Convex Hull Interpolation

Due to the homogeneous signal intensity of intra-chamber structures (e.g., papillary muscles in LV) and the surrounding myocardial tissue, many segmentation techniques exclude these structures from the chamber. Our method identifies these structures and adds them back to the reconstructed volume. For example, in the LV, this modification step applies primarily over the slices encompassing the LV base, since the papillary muscles are thicker in that portion compared to the apical segment of the LV.

For each 2D slice, the algorithm considers the contour obtained from the previous phase. Due to the exclusion of the intra-chamber structures (e.g., papillary muscles in the LV), this contour is non-convex, meaning that the line connecting any two points inside the contour is not necessarily inside the contour. We argue that if this contour's convex hull can be found and the points on the convex border can be interpolated, it should be possible to refine the segmentation. To do so, we will first identify the points on the contour's convex hull, for which various algorithms exist (Franco P. Preparata MIS. Computational Geometry, Chapter "Convex Hulls: Basic Algorithms": Springer: 1985). Next, given this set of points, we compute the centroid by averaging over all the points.

Figure 3:
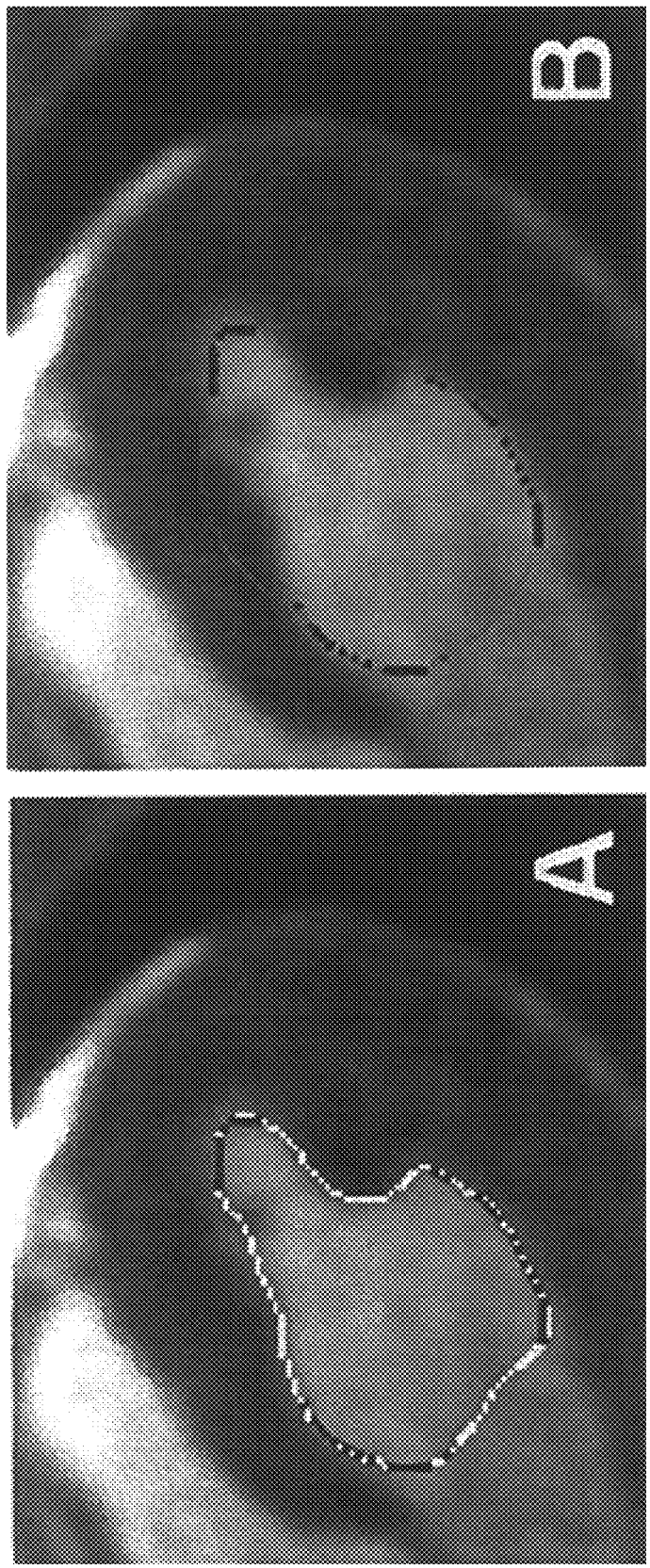
FIG. 3: (A) shows a 2D cross-section of first phase segmentation while (B) shows the convex hull of the segmentation, which includes the papillary muscles (red curves). The blue dots on the LV border specify the convex hull. The red curve illustrates the output of linear interpolation of the blue points in the cylindrical coordinates.
Figure 4:
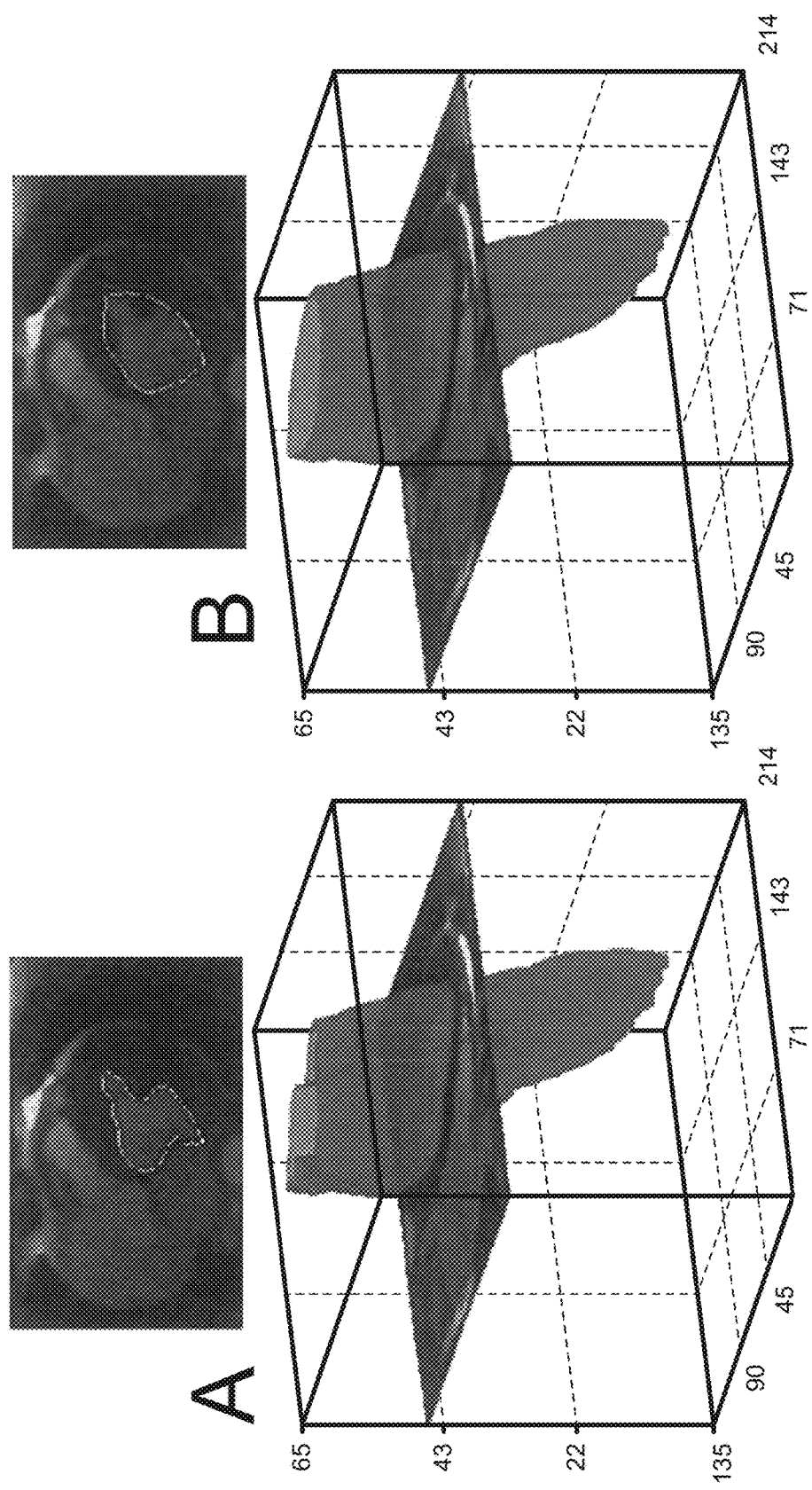
FIG. 4: (A) The 3D segmentation of the left ventricle prior to phase 2, vs. (B) after phase 2 (convex hull interpolation). This figure shows how the papillary muscles are incorporated using the convex hull interpolation. Two cross-sections with and without papillary muscles are provided for better clarification.

This centroid point is used as the center of the cylindrical coordinates, and the radius and angle of all points on the convex hull are calculated based on the new coordinate system. Let $r_1, r_2, \ldots, \Theta_N$ and $\Theta_1, \Theta_2, \ldots, \Theta_N$ denote the radii and angles of these points, respectively, with ri and $\Theta$i representing the distance and angle of ith point with regard to the center. The $\Theta$I s are not equally spaced angles. Once we find the cylindrical coordinates of the convex hull points, we consider the r vs. $\Theta$ scatter plot, and then fit a parabolic curve using piece-wise interpolation so that for equally spaced $\Theta'_1, \Theta'_2, \ldots, \Theta'_M$, we have their corresponding $r'_1, r'_2, \ldots, r'_M$. This new set of points constructs a closed convex curve that best approximates the non-convex chamber contour. This convex curve includes the intra-chamber structures as well as seen in FIGS. 3 and 4. Specifically, FIG. 3A shows a 2D cross section of the first phase segmentation while FIG. 3B shows the convex hull of the segmentation which includes the papillary muscles which are denoted by the red curves. The blue points on the LV border specify the convex hull while the red curve illustrates the output of linear interpolation of the blue points in the cylindrical coordinates. The effect of this modification on LV volume is shown in FIG. 4, in the right panel, which provides a more accurate representation of LV geometry. Specifically, FIG. 4A shows the 3D segmentation of the LV prior to completing step II. FIG. 4B shows the segmentation of the LV after the convex hull interpolation process in step II has been completed. FIG. 4B also shows how the papillary muscles are incorporated using the convex hull interpolation.

Step III: Myocardial Segmentation

Figure 5:
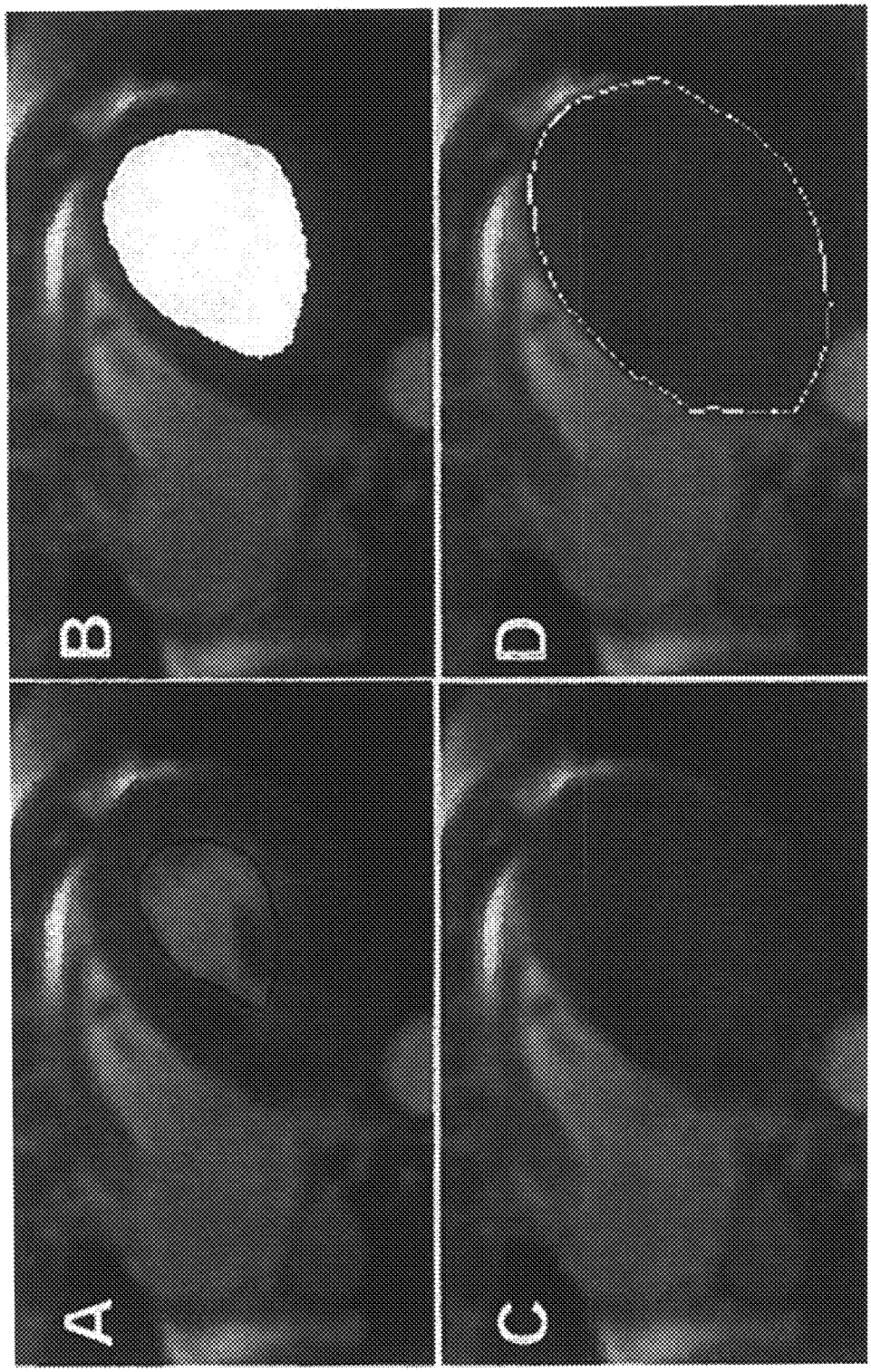
FIG. 5: A cross-section of 3D segmentation procedure during phase III: (A) is a result of phase II; (B) removing the intra-chamber area; (C) refilling with myocardium; (D) white line shows enclosing left ventricle with all of its contents (two-chamber view).

This step extracts the enclosing myocardium (as the foreground) from the rest of the CMR image. We follow the 3D segmentation method discussed in step I with some image manipulation and slight changes in external energy functions. Once the enclosing chamber is segmented (as in step I) and its boundaries are detected from the first phase, the algorithm removes the endocardium and refills it with the color of the myocardium, which surrounds the chamber. This process is shown in FIG. 5.

The hull of FIG. 5B shows the area that should be refilled with the color intensity of myocardium. To do so, the algorithm moves a few pixels away from the endocardial boundary and then performs the refilling procedure. This expansion from the endocardial boundary in FIG. 5A to FIG. 5B ensures that the algorithm does not overlook any endocardial pixels. Additionally, it allows the segmentation to reach to the region of the myocardium and use its color for refilling. In order to refill, we interpolate inward using the color densities through solving the Laplace's equation. This novel method of refilling produces a homogeneous region of segmented myocardium that includes the endocardium as seen in FIG. 5C. The white line in FIG. 5D encloses the LV with all of its contents.

Next, the algorithm applies the same 3D segmentation method previously discussed in step I to find the borders of the endocardium. However, unlike the segmentation process in step I, we have a rough estimate of the density histogram distribution of the foreground (enclosing myocardium) and background (the rest of the heart). We pick some sample voxels of myocardium without user interaction. This is possible because we know that the myocardium surrounds the LV cavity and from the previous step we know the location of the LV cavity. Furthermore, the approximate thickness of the myocardium of the LV is known. Hence, to find the myocardium (foreground) sample pixels, we simply need to move slightly away from the convex hull points found in step II and pick some samples of myocardium. To find the background sample points, the focus would be on the points far from the centroid point. We move along the radial lines of the equally spaced angles obtained in the previous stage to obtain both foreground and background sample points.

Once these sample voxels are known, we find the foreground and background PDFs ($p(\bullet|\Omega_F)$ and $p(\bullet|\Omega_B)$) in a region-based term. We consider a Gaussian mixture model with K=3 Gaussian components $N(x; m_{is}, \sigma^2)$ to represent $p(\bullet|\Omega_F)$ and $p(\bullet|\Omega_B)$, i.e., $$p(I(v)|\Omega_s) = \sum_{i=1}^{K} \frac{\omega_{is}}{\sigma_{is}\sqrt{2\pi}} e^{-\frac{(I(v)-m_{is})^2}{\sigma_{is}^2}}, \quad (9)$$

$$s \in \{F, B\}$$

with parameters ($\Omega_{is}$, $m_{is}$, $\sigma_{is}^2$ representing the weight, the mean, and the variance of the $i^{th}$ component of foreground (s=F) and background (s=B). These parameters can be identified using the expected maximization (EM) method (Dempster A P, Laird N M, Rubin D B. Maximum likelihood from incomplete data via the EM algorithm. *Journal of the Royal Statistical Society Series B (Methodological)* 1977:1-38) from the sample voxels obtained earlier.

Figure 6:
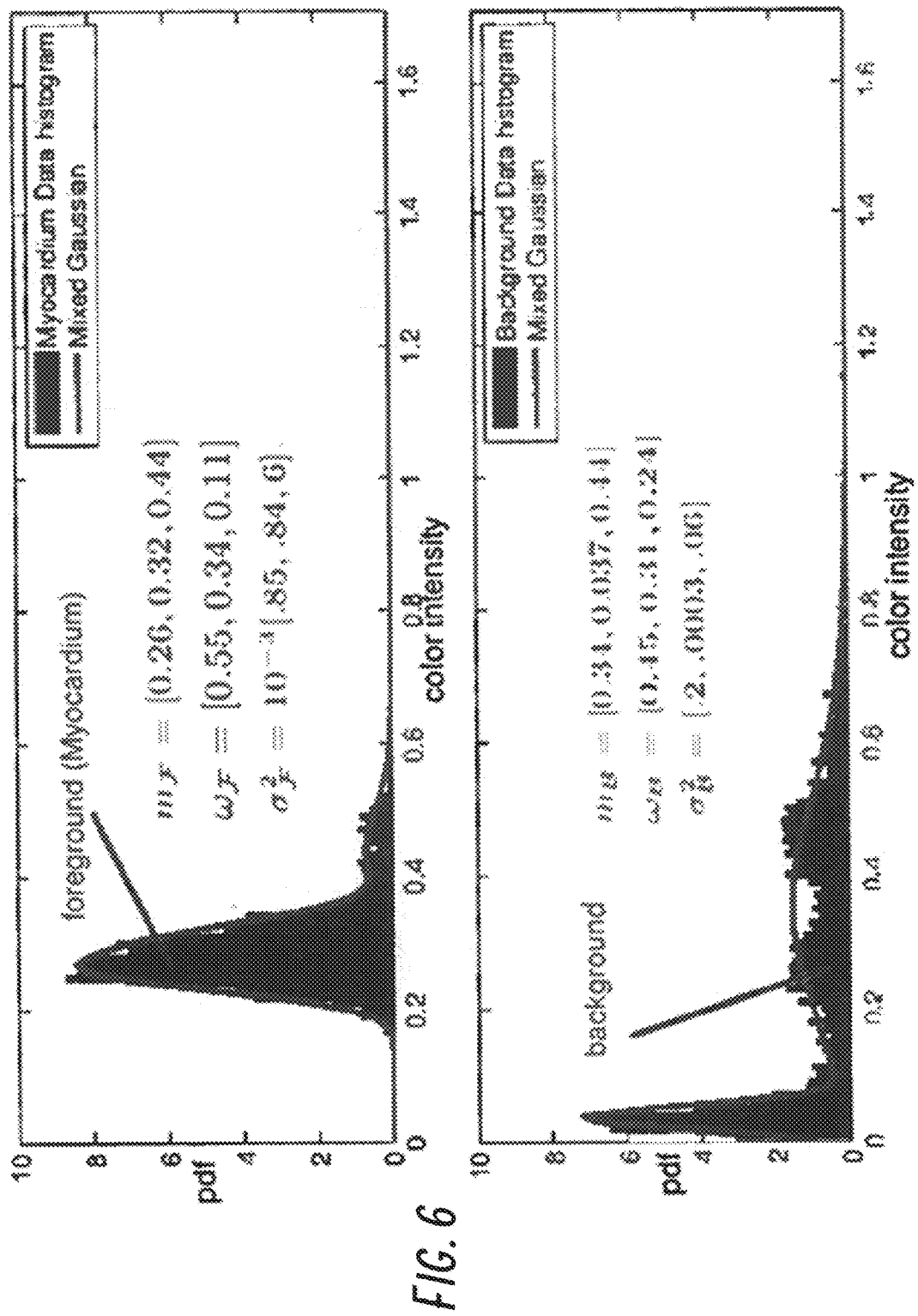
FIG. 6: PDF estimation of histogram sample of myocardium and the background using EM method.
Figure 7:
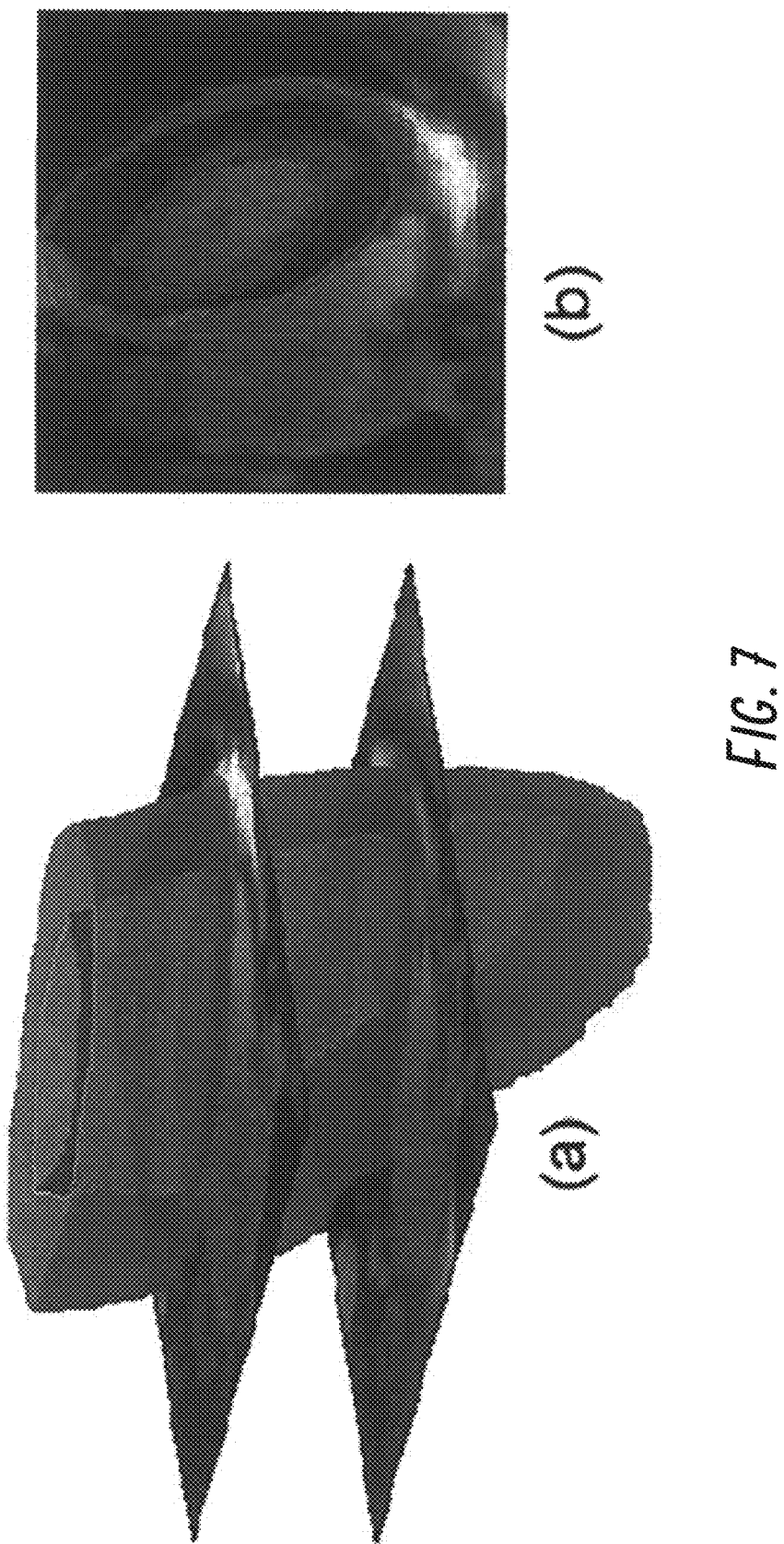
FIG. 7: (a) Volumetric segmentation of the left ventricle; (b) top view.

FIG. 6 depicts a histogram sample of myocardium and the background using the EM method. It also shows how the estimated Gaussian mixture model with obtained parameters fits this histogram. We note that once the PDF parameters are determined, they remain fixed over all iterations and unlike the step I procedure, there is no need to update them. The result of this phase is shown FIG. 7, specifically with FIG. 7A showing the volumetric segmentation of the LV and FIG. 7B showing a top view of the same.

To validate our algorithm, we took a multi stage approach. The first stage was a direct comparison to manually segmented images, the second was a comparison to two other automated techniques, and the third was a phantom experiment. Finally, in the fourth stage we tested the effect changes in contrast to noise ratio (CNR), signal to noise ratio (SNR) and MRI slice thickness on the algorithm.

For initial validation purposes, we compared a single volume of the object (LV) obtained from manual segmentation, $V_{man}$, with the data obtained from our automatic technique $V_{auto}$. To compute the volume, we employed Simpson's rule. This method needs to include the pixel-spacing and slice-spacing of the 3D image, which was extracted from the CMR data. We also used Dice metric given by $$\frac{2V_{man} \times V_{auto}}{V_{man} + V_{auto}}.$$

This metric is in fact the F1 metric in the context of machine learning. Our algorithm was examined on a CMR dataset from the Department of Diagnostic Imaging of the Hospital for Sick Children in Toronto, Canada, available from the York University website.

To further test the functionality of our algorithm in an objective manner, we compared its performance with that of two popular automatic cardiac segmentation methods on the York database. The first method we chose was developed by Grosgeorge et al. (Grosgeorge D, Petitjean C, Caudron J, Fares J, Dacher J-N. Automatic cardiac ventricle segmentation in MR images: a validation study. *International journal of computer assisted radiology and surgery* 2011; 6(5): 573-581) and the second method was developed by Mille (Mule J, Bone R, Makris P, Cardot H. Segmentation and tracking of the left ventricle in 3D MRI sequences using an active surface model. In *Computer-Based Medical Systems, Twentieth IEEE International Symposium on*; 2007. p. 257-262) and Pluempitiwiriyawej (Pluempitiwiriyawej C, Moura J M F, Wu Y-J L, Ho C. STACS: new active contour scheme for cardiac MR image segmentation. *Medical Imaging, IEEE Transactions on* 2005; 24(5): 593-603). Grosgeorge's method employs an active model without either an edge term or a geometric term. Moreover, the same variance is assumed for the foreground (LV) and background (rest of the CMR image) probability distribution functions. Our method differs by considering the foreground and background as belonging to two different texture regions, thus adopting different variances, which we feel is more appropriate. Mille (supra) and Pluempitiwiriyawej (supra) developed similar methods. Both methods consider an edge-based term and a region-based term but not a geometric term. Pluempitiwiriyawej (supra) assumes a general geometry-based term, which it is not applicable here. Neither of the methods used for comparison employ histogram matching or convex-hull interpolation.

Figure 8:
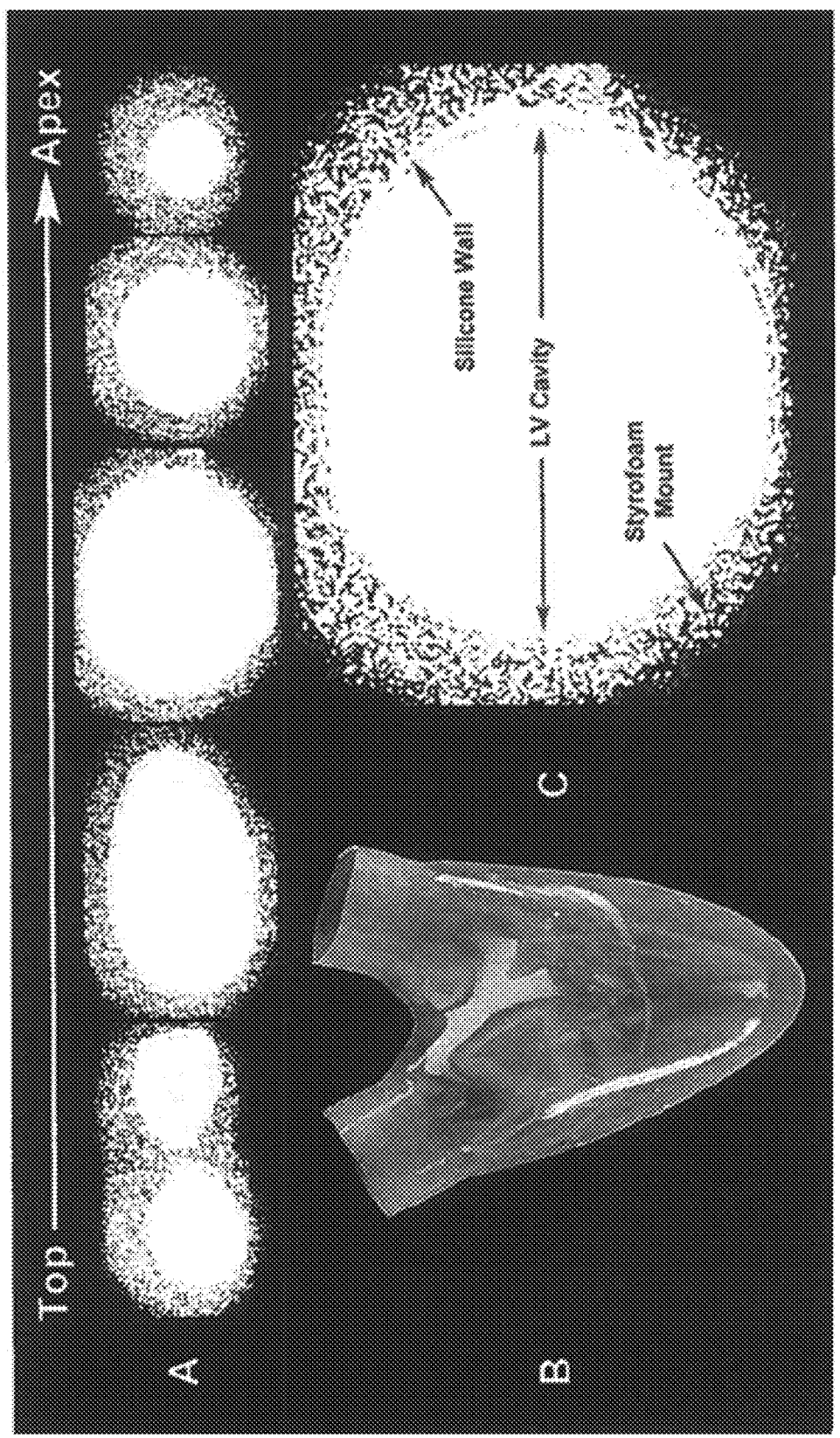
FIG. 8: (A) Top to apical view of select short axis MRI slices of the phantom. (B) The silicone model of the left ventricle used as a phantom in this experiment. (C) A mid ventricle slice with the components of the phantom labeled.

In order to estimate the absolute accuracy of our segmentation method, a phantom was constructed with a known volume. The phantom is a simulation of a human left ventricle including an inlet and an outlet as seen in FIG. 8. FIG. 8A shows a top to apical view of select short axis MRI slices of the phantom. FIG. 8B illustrates the silicone model of the LV used as a phantom in the experiment. Finally, FIG. 8C shows a mid ventricle slice with the components of the phantom labeled. It is composed of transparent silicone rubber and shaped according to molds of a human left ventricle in the systolic state. Our phantom was filled with 330 mL of water mixed with 2 mL of gadolinium, then held in a Styrofoam mold to keep it in place inside the MR scanner. The phantom was imaged on a Phillips Medical System Achieva 3T scanner with a breast coil. The image dimensions were 512×512 and 2D images were acquired at slice thicknesses and x and y spacing, respectively, of 1 mm, 0.234 and 0.235 mm. FIG. 8 is a composite image of the phantom and the corresponding MR images. After obtaining the 3D segmentation of the phantom, we used Simpson's rule to obtain the volume and compare it to the known phantom volume of 332 mL. Examining the effects of changes in CNR and SNR was accomplished by introducing additive noise to one of the available MRI dataset (in this example, we choose patient 29 of the York database) and examined how the algorithm's performance changes as CNR and SNR decrease. Patient 29 was chosen as this study was of very high quality and thus a considerable amount of noise could be added before the study was uninterpretable.

To measure the effect of MRI slice thickness on our algorithm, we took the same dataset (i.e., #29) and performed a segmentation of the right ventricle using the original slice thickness of 1.6 mm. To account for changes in slice thickness, we then repeated the segmentation only considering a subset of slices; first only utilized every other slice in the stack thus the effective slice thickness was twice the original slice thickness, i.e., 3.2 mm. This procedure was repeated using every third slice (slice thickness 4.8 mm), then every fourth slice (slice thickness 6.4 mm), etc. The segmentation algorithm was applied on all these stacks, and the F1 accuracy performances were compared.

Figure 9:
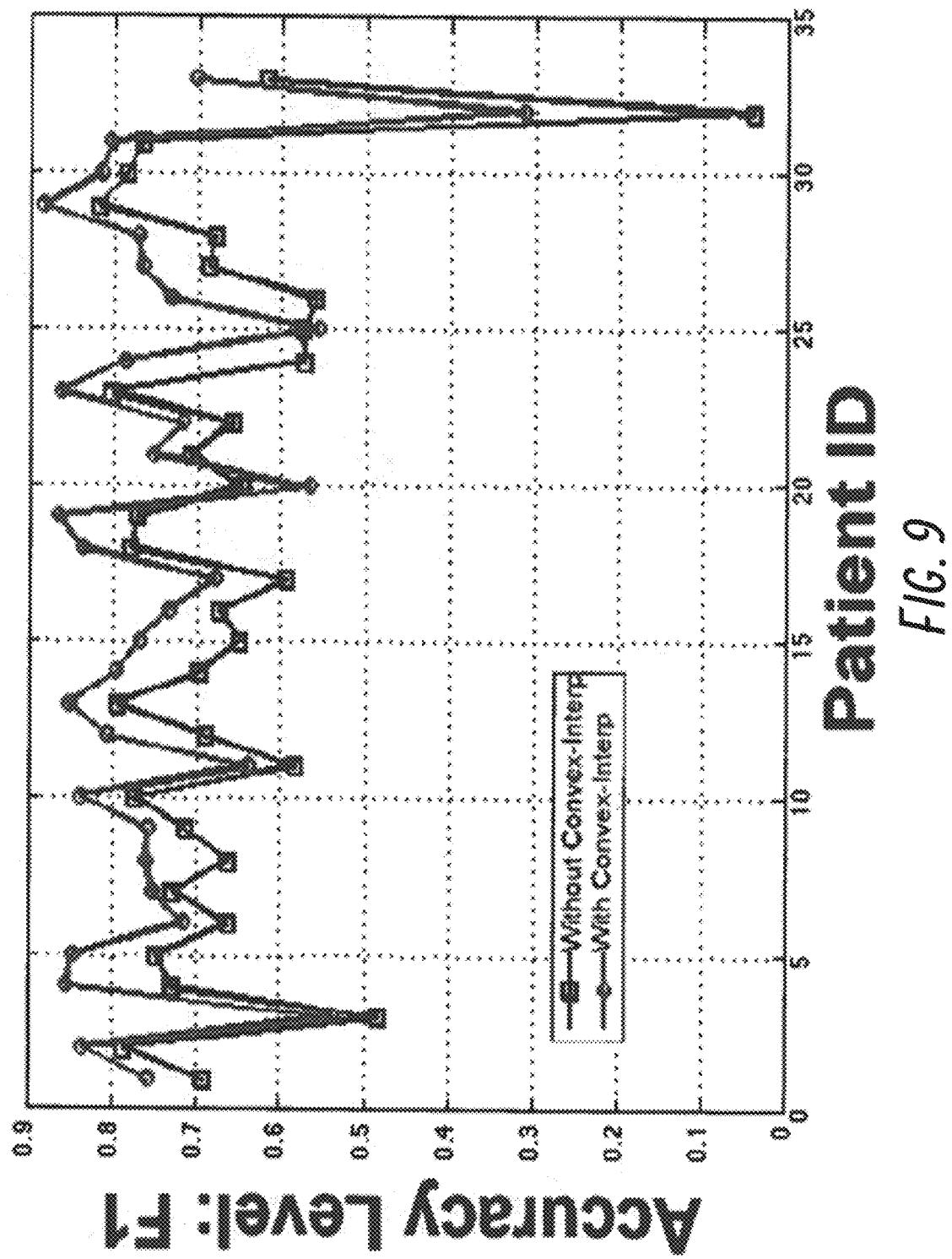
FIG. 9: Accuracy of our algorithm for different patients in York dataset.

In segmenting the left ventricle, we achieved between 80% to 90% accuracy in estimating the LV volume in 13 of the cases when compared to the supplied manual segmentation volumes, and in only 5 cases did our estimate fell below 70%. FIG. 9 depicts the accuracy (dice metric) of our method both with and without convex-hull interpolation versus the patient's manually segmented volume. We observe that the convex hull interpolation improves the accuracy by almost 10%. With this improvement, our results are very accurate considering that our segmentation method relies on no training data set.

As the FIG. 9 shows, our algorithm performs robustly for almost all 33 subjects of York database except for patient #32 whose segmentation result was suboptimal. The reason for the inferior performance in this one particular case was likely due to the very poor nature of the study. This study had a very low CNR and SNR, which results in unclear borders that in turn causes contour leakage and poor segmentation performance.

Figure 10:
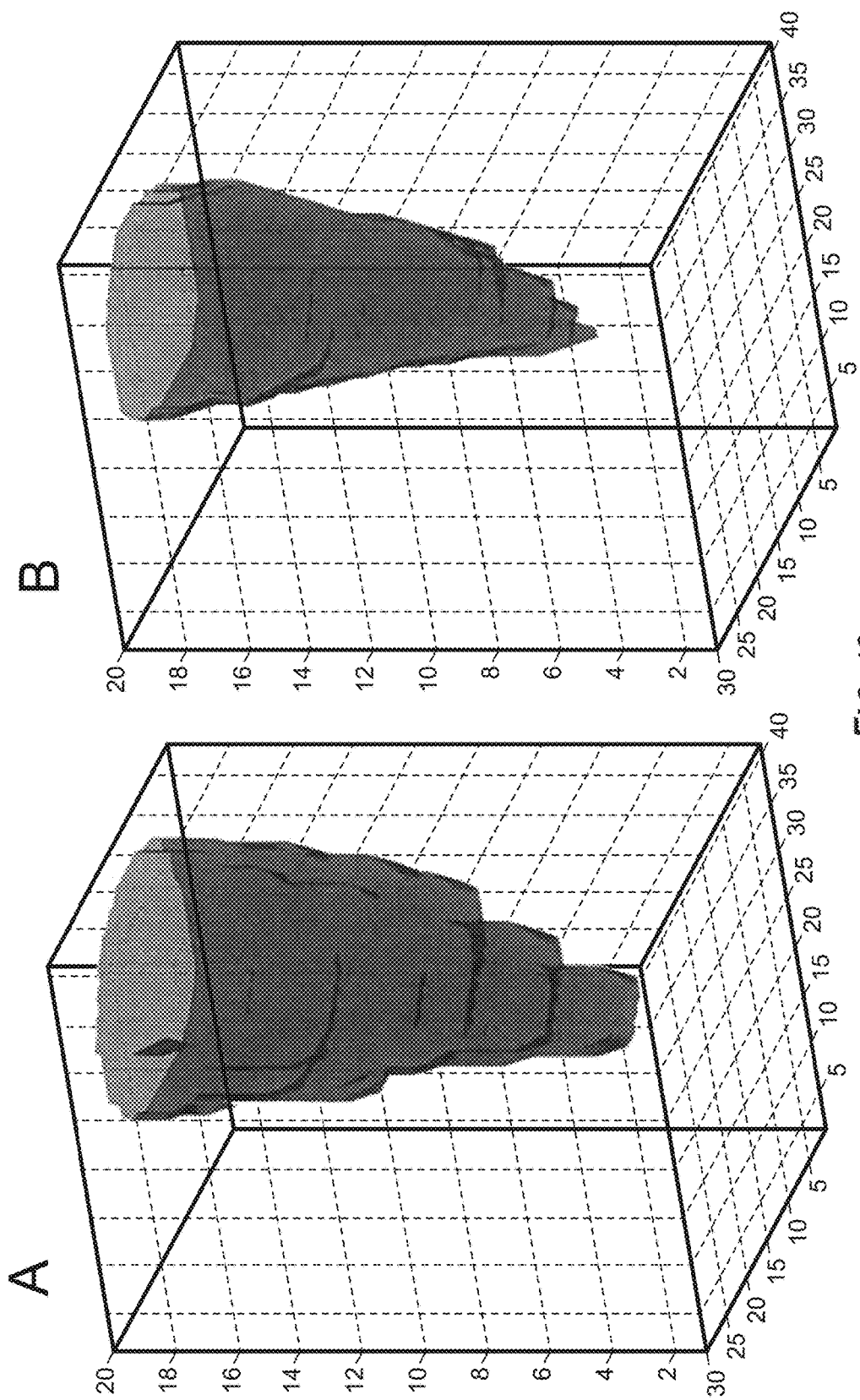
FIG. 10: Manual segmentation by a trained operator (left) vs. our method's output (right) for patient 11 of York dataset.

FIG. 10 illustrates that a 3D model of the left ventricle obtained from our method looks much smoother than the manual segmentation result provided by the challenge organizer that was utilized as the gold standard. As seen in FIG. 10, the left panel shows manual segmentation by a trained operator while the right panel shows the current method's output for patient #11 of the York dataset. This may indicate that our algorithm is far more accurate compared to the presented data, not because smoothness inherently implies accuracy, but because there are obvious discontinuities in the manual segmentation that misrepresent the shape of the left ventricle. The manual segmentation is inherently inaccurate, and several studies have shown that manual segmentation can be grossly imprecise with a low level of reproducibility (Kadir K A, Payne A, Soraghan J J, Berry C. Automatic left ventricle segmentation in T2 weighted CMR images. In *Image Processing and Communications Challenges* 2: Springer; 2010. p. 247-254; Sardanelli F, Quarenghi M, Di Leo G, Boccaccini L, Schiavi A. Segmentation of cardiac cine MR images of left and right ventricles: interactive semiautomated methods and manual contouring by two readers with different education and experience. *Journal of Magnetic Resonance Imaging* 2008; 27(4): 785-792).

Figure 11:
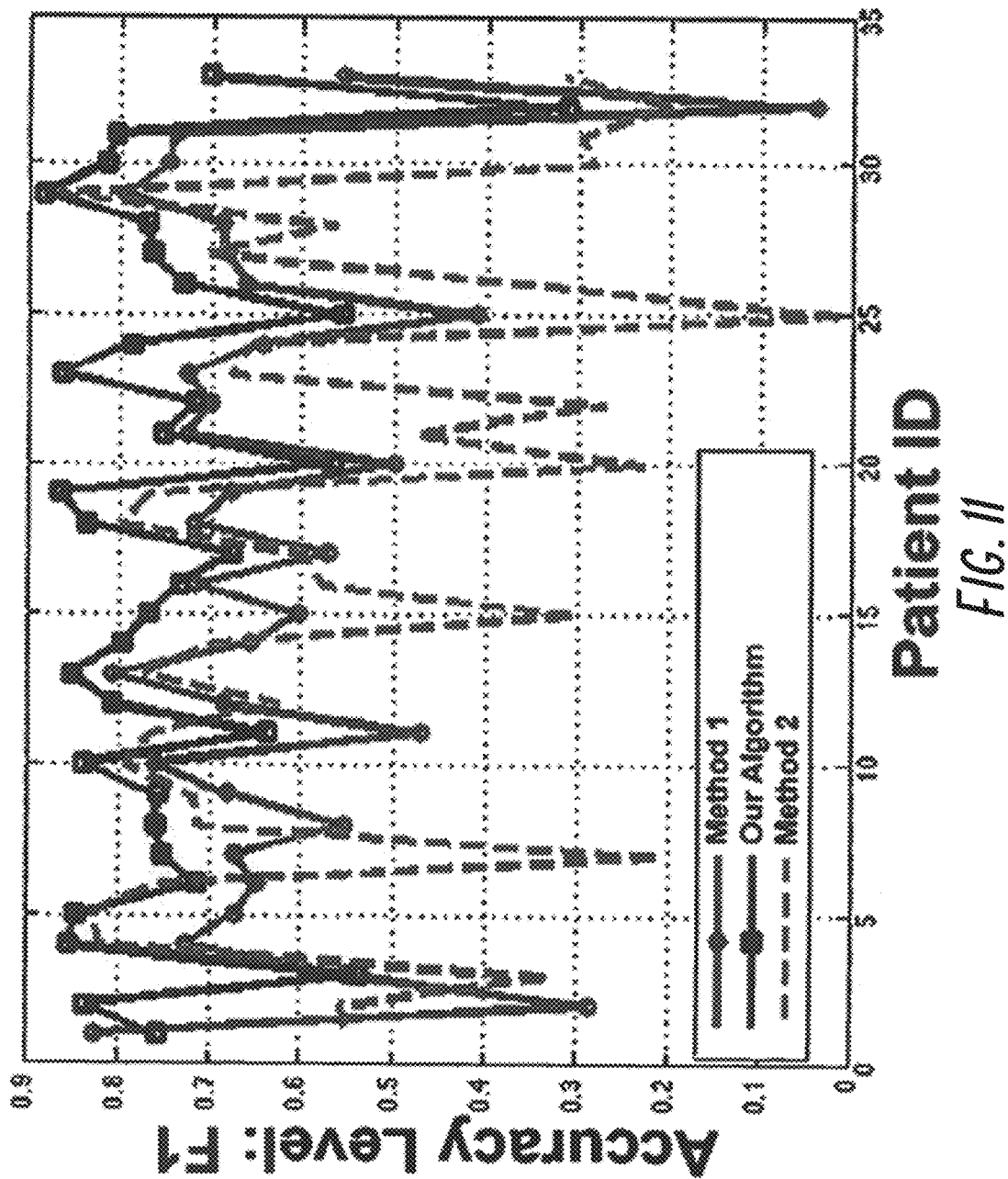
FIG. 11: Accuracy for different patients in York dataset for our algorithm as well as other existing algorithms. Method 1 was developed by Grosgeorge et al. (Grosgeorge D, Petitjean C, Caudron J, Fares J, Dacher J-N. Automatic cardiac ventricle segmentation in MR images: a validation study. *International journal of computer assisted radiology and surgery* 2011; 6(5): 573-581) and method 2 by Mule et al. (Mule J, Bone R, Makris P, Cardot H. Segmentation and tracking of the left ventricle in 3D MRI sequences using an active surface model. In *Computer-Based Medical Systems, Twentieth IEEE International Symposium on;* 2007. p. 257-262) and Pluempitiwiriyawej et al. (Pluempitiwiriyawej C, Moura J M F, Wu Y-J L, Ho C. STACS: new active contour scheme for cardiac MR image segmentation. *Medical Imaging, IEEE Transactions on* 2005; 24(5): 593-603).

In FIG. 11 we have depicted the F1 accuracy of our algorithm compared to the other two methods described above for patients from the York database. Our algorithm outperforms the pre-existing algorithms (Grosgeorge D, Petitjean C, Caudron J, Fares J, Dacher J-N. Automatic cardiac ventricle segmentation in MR images: a validation study. *International journal of computer assisted radiology and surgery* 2011; 6(5): 573-581; Mule J, Bone R, Makris P, Cardot H. Segmentation and tracking of the left ventricle in 3D MRI sequences using an active surface model. In *Computer-Based Medical Systems, Twentieth IEEE International Symposium on;* 2007. p. 257-262; and Pluempitiwiriyawej C, Moura J M F, Wu Y-J L, Ho C. STACS: new active contour scheme for cardiac MR image segmentation. *Medical Imaging, IEEE Transactions on* 2005; 24(5): 593-603) in almost every case, with substantial improvement in most cases.

As mentioned previously, we conducted a reproducibility study on an LV phantom with a known volume of 332 mL. We independently ran the algorithm 10 times, each instance with different randomly distributed initial point. We set the termination condition of algorithm to 700 iterations or less than $10^{-4}$% change in each iteration. Given these conditions, the 3D results took roughly 2 minutes to generate. Our algorithm returned values between 325 mL and 364 mL with a mean value of 3452±10.5 mL. These values correspond to an average error of 3.97%±3.16% with a maximum error of 9.63% produced by the value of 364 mL which was somewhat of an outlier.

Figure 12:
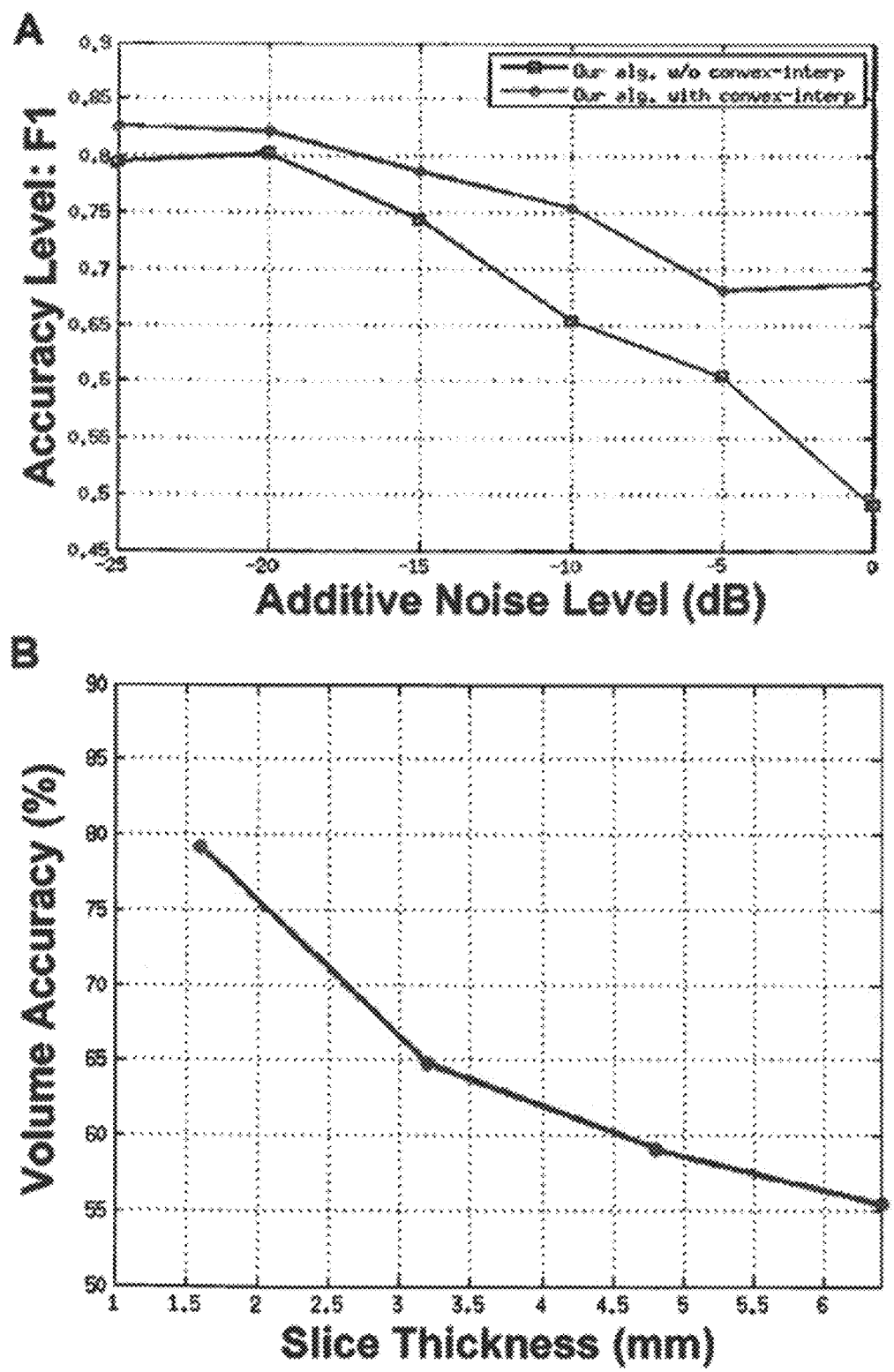
FIG. 12: (A) The performance of our algorithm with and without convex-hull interpolation vs. various level of additive noise for patient 29. (B) The RV F1 accuracy performance of our segmentation algorithm versus the slice thickness.

FIG. 12A depicts a plot of the performance of our algorithm with and without convex hull interpolation as a function of various levels of additive noise. Predictably, performance drops as the level of noise increases, or inversely, when the SNR or CNR decreases. However, the performance stays relatively constant until more than −20 dB of added noise, indicating the algorithm is robust. It must be noted that it is not generally straightforward to report an operating CNR or SNR for these type of studies. The reason is that there are other parameters involved in the performance, directly correlated with CNR, such as SNR, the weighting parameters, or initialization of our algorithm that makes it hard to give a number for operating CNR. Finally, the introduction of significant noise (>−10 dB) did make the performance of the algorithm considerably decline; however, that degree of noise would likely render a study uninterpretable regardless of the method of segmentation.

FIG. 12B also depicts the F1 accuracy performance versus the slice thickness for RV segmentation. As expected, the performance drops as the slice thickness increases and the gap between two slices widens so that 30% drop is observed once the gap increases by the factor of 3.

Magnetic resonance imaging has been a mainstay in clinical practice for some time. Initially used to primarily image the stationary organs, techniques such as gating and respiratory motion suppression have improved imaging quality to the point where MR imaging has become a very useful tool for the diagnosis of a host of cardiovascular pathologies (Groves E M, Bireley W, Dill K, Carroll T J, Carr J C. Quantitative analysis of ECG gated high-resolution contrast-enhanced MR angiography of the thoracic aorta. *American Journal of Roentgenology* 2007; 188(2): 522-528). As discussed above, obtaining an accurate segmentation in CMR to determine relevant clinical information is critical, and currently due to the heavy reliance on manual segmentation, results can be inaccurate with a high intraobserver viability (Janik M, Cham M D, Ross M I, et al. Effects of papillary muscles and trabeculae on left ventricular quantification: increased impact of methodological variability in patients with left ventricular hypertrophy. *Journal of hypertension* 2008; 26(8):1677-1685). There is currently a paucity of automated segmentation techniques and those that do exist have significant limitations.

The current automated segmentation approach is model-based and incorporates prior knowledge about the object that relies on a statistical model created from a large database of manually-segmented images. Active appearance model (AAM) (Mitchell S C, Bosch J G, Lelieveldt B P F, van der Geest R J, Reiber J H C, Sonka M. 3-D active appearance models: segmentation of cardiac MR and ultrasound images. *Medical Imaging, IEEE Transactions on* 2002; 21(9): 1167-1178) and active shape model (ASM) (Van Assen H C, Danilouchkine M G, Frangi A F, et al. SPASM: a 3D-ASM for segmentation of sparse and arbitrarily oriented cardiac MRI data. *Medical Image Analysis* 2006; 10(2):286-303; Kaus M R, Berg J v, Weese J, Niessen W, Pekar V. Automated segmentation of the left ventricle in cardiac MRI. *Medical Image Analysis* 2004; 8(3): 245-254) are two popular model-based techniques. Another relevant algorithm (Lorenzo-Valdes M, Sanchez-Ortiz G, Mohiaddin R, Rueckert D. Segmentation of 4D Cardiac MR Images Using a Probabilistic Atlas and the EM Algorithm. In *Medical Image Computing and Computer-Assisted Intervention-MICCAI* 2003; 2003. p. 440-450) uses the expectation maximization (EM) algorithm to make a cardiac 4D probabilistic atlas, which computes the probabilities that a voxel belongs to a certain region in the heart. On that basis, others (Ulen J, Strandmark P, Kahl F. An Efficient Optimization Framework for Multi-Region Segmentation based on Lagrangian Duality. *IEEE transactions on medical imaging* 2012) utilize focusing on a set of 2D CMR images, developed a multi-region segmentation model that maps the segmentation problem to a max flow-mm cut problem in graph theory.

Overall, the model-based approaches demonstrate adequate segmentation performance once the dataset is sufficiently large (Bresson X, Vandergheynst P, Thiran J-P. A variational model for object segmentation using boundary information and shape prior driven by the Mumford Shah functional. *International Journal of Computer Vision* 2006; 68(2): 145-162). Small datasets incur a large bias to the segmentation, making these methods ineffective when the heart shape is outside the learning set, which is likely to occur in the case of cardiovascular diseases since the learning sets are primarily composed of normal images. Yet another challenge is to obtain large segmented datasets, which must be addressed using model-based approaches. Therefore, it is believed that model-based methods are not feasible, as they are likely to result in significant error if the algorithm is applied to cases beyond the original dataset (Bresson et al. (supra)). Another limitation of model-based algorithms is that the training data must be in the same format as the test data; for example, if the training data are constructed using short-axis CMR images, they cannot be used for long-axis image segmentation.

In order to progress beyond the statistical model, several other approaches have been taken such as thresholding (Goshtasby A, Turner D A. Segmentation of cardiac cine MR images for extraction of right and left ventricular chambers. *Medical Imaging, IEEE Transactions on* 1995; 14: 56-64), pixel classification (Pednekar A, Kurkure U, Muthupillai R, Flamm S, Kakadiaris I A. Automated left ventricular segmentation in cardiac MRI. *Biomedical Engineering, IEEE Transactions on* 2006; 53(7): 1425-1428; Lynch M, Ghita O, Whelan P F. Automatic segmentation of the left ventricle cavity and myocardium in MRI data. *Computers in Biology and Medicine* 2006; 36(4): 389-407) and active contour (Xu C, Pham D L, Prince J L. Image segmentation using deformable models. *Handbook of medical imaging* 2000; 2:129-174; Grosgeorge D, Petitjean C, Caudron J, Fares J, Dacher J-N. Automatic cardiac ventricle segmentation in MR images: a validation study. *International journal of computer assisted radiology and surgery* 2011; 6(5): 573-581). Others have developed an algorithm for automated segmentation of left ventricle known as (LV-METRIC) (Codella N C, Weinsaft J W, Cham M D, Janik M, Prince M R, Wang Y. Left ventricle: automated segmentation by using myocardial effusion threshold reduction and intravoxel computation at MR imaging. *Radiology* 2008; 248(3): 1004). This method estimates the mean and standard deviation of LV and myocardium signal intensities through region-growing method and calculate the volume of LV by selecting an appropriate threshold. A clinical validation study was conducted on this method (Codella N C, Cham M D, Wong R, et al. Rapid and accurate left ventricular chamber quantification using a novel CMR segmentation algorithm: a clinical validation study. *Journal of Magnetic Resonance Imaging* 2010; 31(4): 845-853). While this method results in a good performance in calculating volume, it does not guarantee the object coherency and the result may have holes. These issues are addressed in active contour methods. Active contours are curves or surfaces that evolve and move toward the object of interest driven by two forces: one internal and the other external. While the internal force attempts to keep the contour smooth during evolution, the external force is responsible for stopping the contour around the object of interest. The internal force is a function of the contour itself, in contrast to the external forces, which are obtained from the image data. Although most methods assume a common internal force, their external forces differ. For instance, several investigators have adopted the edge-based external force, defined as the gradient of image that stops the contour at the edges (Xu C, Pham D L, Prince J L. Image segmentation using deformable models. *Handbook of medical imaging* 2000; 2:129-174; El Berbari R, Bloch I, Redheuil A, et al. An automated myocardial segmentation in cardiac MRI. Engineering in Medicine and Biology Society, 29th Annual International Conference of the IEEE; 2007. p. 4508-4511; and Mora M, Tauber C, Batatia H. 2D local heart motion estimation using level sets and hierarchical B-splines. In *Computers in Cardiology;* 2006. p. 513-516). The drawback of such methods is that since the low contrast between neighboring anatomic structures causes CMR images to have poorly-defined borders, these methods' stopping conditions may fail to work properly when stopping the contour.

To address this issue, other groups have employed a region-based approach (Grosgeorge D, Petitjean C, Caudron J, Fares J, Dacher J-N. Automatic cardiac ventricle segmentation in MR images: a validation study. *International journal of computer assisted radiology and surgery* 2011; 6(5): 573-581; Mule J, Bone R, Makris P, Cardot H. Segmentation and tracking of the left ventricle in 3D MRI sequences using an active surface model. In *Computer-Based Medical Systems, Twentieth IEEE International Symposium on;* 2007. p. 257-262; and Chan T F, Vese L A. Active contours without edges. Image Processing, *IEEE Transactions on* 2001; 10(2): 266-277) for CMR images and shown to offer more robustness. Others (Pluempitiwiriyawej C, Moura J M F, Wu Y-J L, Ho C. STACS: new active contour scheme for cardiac MR image segmentation. *Medical Imaging, IEEE Transactions on* 2005; 24(5): 593-603) have considered a linear combination of the region-based and edge-based forces and proposed an annealing schedule to balance these factors' weight in their model. The current invention is a 3D version of this concept for the left ventricle (LV) and myocardial segmentation. To improve the model's robustness, we also incorporate geometrical constraints (Wang T, Han B, Collomosse J. TouchCut: Fast image and video segmentation using single-touch interaction Computer Vision and Image Understanding 2013; In process).

Through rigorous calculation, the LV chamber and myocardium were accurately segmented in 3D for thirty three MRI datasets. Our method is robust and demonstrated a high segmentation performance when compared to manual segmentation. The reproducibility study on a left ventricle phantom with a known volume resulted in an average error of 3.97%±3.16%.

We have successfully developed a novel 3D segmentation algorithm that can reconstruct a cardiac chambers' morphology for use in quantitative analyses. The algorithm is widely applicable, is fast and results in reproducible data.

Since our algorithm uses no manual segmenting, it is highly reproducible, while also not requiring a training data set, or any user driven segmentation to make it fully 3D. As a result, when compared to previously developed technologies, we showed a high level of performance without the use of a training data set that was utilized in many other\algorithms. Our method demonstrates much less performance variation and shows more robustness in the results compared to others. This consistency is mainly due to the geometric term considered in our external force. Additionally, application of a convex hull interpolation and histogram matching are critical components of our algorithm.

Automated segmentation algorithms generally utilize assumptions that may be inaccurate across heterogeneous populations. Here we have progressed beyond the need for such limitations and thus have described an algorithm which does not rely upon a training data set. With more accurate, reproducible segmentation results, CMR can be relied upon more heavily both in the initial diagnosis of cardiovascular disease, but also in the monitoring of progression which is critical in management.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

The words used in this specification to describe the invention and its, various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in must be understood as being generic to all possible meanings supported by the specification and by the word itself.

The definitions of the words or elements of the following invention and its various embodiments are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the invention and its various embodiments below or that a single element may be substituted for two or more elements in a claim.

Insubstantial changes from the claimed subject matter as viewed by a person with ordinary skill in the art, now known or later devised, are expressly contemplated as being equivalently within the scope of the invention and its various embodiments. Therefore, obvious substitutions now or later known to one with ordinary skill in the art are defined to be within the scope of the defined elements.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A method of automatically producing a three-dimensional (3D) segmentation of a heart chamber, the method comprising:
   (a) obtaining data sets from cardiac magnetic resonance imaging (MRI) or ultrasound,
   (b) generating a 3D segmentation of the heart chamber from the data sets using an active contour method comprising minimizing an energy function, $E(\Phi)$, when a contour lies on a boundary of the heart chamber, wherein $E(\Phi)$ is defined as $$E(\Phi)=E_{int}(\Phi)+E_{ext}(\Phi),$$

wherein $E_{int}$ is the internal energy function and $E_{ext}$ is the external energy function of the heart chamber in a 3D domain,
   (c) modifying the 3D segmentation by adding a plurality of intra-chamber structures; and
   (d) identifying an enclosing myocardium using the 3D segmentation generated in step (b).

2. The method of claim 1, where minimizing the energy function, $E(\Phi)$ comprises using an external energy function, $E_{ext}(\Phi)$, defined as $$E_{ext}(\Phi)=w_2E_{reg}+w_3E_{edge}+w_4E_{geom}$$

wherein $E_{reg}$ is a region-based term, $E_{edge}$ is an edge-based term, $E_{geom}$ is a geometric term, and where $w_2$, $w_3$, and $w_4$ are a plurality of weighting parameters.

3. The method of claim 2, further comprising normalizing the MRI or ultrasound data sets and reusing the same weighting parameters across the entire MRI or ultrasound data set.

4. The method of claim 1, where the MRI or ultrasound data sets comprise short-axis cardiac magnetic resonance images, long-axis cardiac magnetic resonance images, sagittal MRI images, coronal MRI images, axial MRI images, or any combination thereof.

5. The method of claim 1, where modifying the 3D segmentation by adding a plurality of cardiac substructures comprises:
   identifying a plurality of points on a convex hull of the 3D segmentation;
   computing a centroid for the plurality of points;
   calculating the radius and angle of the plurality of points on the convex hull with respect to the centroid to produce cylindrical coordinates for the plurality of points on the convex hull; and
   interpolating the cylindrical coordinates to produce a closed convex curve which includes the plurality of cardiac substructures.

6. The method of claim 5, where identifying an enclosing myocardium using the 3D segmentation comprises removing a portion of endocardium of the cardiac structure from the 3D segmentation and refilling the 3D segmentation with a pattern representing the myocardium of the cardiac structure in its place as the distance from the centroid is increased.

7. The method of claim 1, where generating a 3D segmentation of the cardiac structure from the MRI or ultrasound data sets comprises simultaneously segmenting the MRI or ultrasound data sets and reconstructing 3D images therefrom.

8. The method of claim 1, wherein said heart chamber is selected from the group consisting of the left ventricle, the right ventricle, the left atrium and the right atrium.

9. The method of claim 1, wherein said modifying the 3D segmentation by adding a plurality of intra-chamber structures comprises adding papillary muscles to a reconstructed volume.

10. The method of claim 1, wherein a 3D contour of the heart chamber is non-convex, wherein a line connecting any two points inside the contour is not necessarily inside the contour, the method comprising identifying points on a convex hull of a contour, computing a centroid value by averaging over all the points, wherein the centroid point is used as a center of cylindrical coordinates and a radius and angle of all points on the convex hull are calculated based on a new coordinate system, wherein a new set of points constructs a closed convex curve that best approximates the non-convex contour.

11. The method of claim 1, further comprising extracting the enclosing myocardium from the rest of the 3D segmentation of the heart chamber.

12. The method of claim 1, further comprising calculating a volume of the heart chamber.

13. A non-transitory computer readable medium containing software instructions for preforming the method of claim 1.

* * * * *